(12) United States Patent
de la Rama et al.

(10) Patent No.: US 6,246,914 B1
(45) Date of Patent: Jun. 12, 2001

(54) HIGH TORQUE CATHETER AND METHODS THEREOF

(75) Inventors: Alan de la Rama, Cerritos; Hosheng Tu; Cary Hata, both of Tustin, all of CA (US)

(73) Assignee: Irvine Biomedical, Inc., Irvine, CA (US)

( * ) Notice: Subject to any disclaimer, the term of this patent is extended or adjusted under 35 U.S.C. 154(b) by 0 days.

(21) Appl. No.: 09/372,484

(22) Filed: Aug. 12, 1999

(51) Int. Cl.⁷ ........................................................ A61N 1/06
(52) U.S. Cl. .......................... 607/122; 604/280; 607/101
(58) Field of Search ................................... 607/122–128, 607/101; 604/280, 282, 94, 95; 600/373–381; 606/41

(56) References Cited

U.S. PATENT DOCUMENTS

| | | | |
|---|---|---|---|
| 5,005,587 | 4/1991 | Scott | 128/786 |
| 5,477,856 * | 12/1995 | Lundquist | 128/642 |
| 5,685,868 * | 11/1997 | Lundquist | 604/280 |
| 5,741,429 * | 4/1998 | Donadio, III et al. | 216/8 |
| 5,766,224 | 6/1998 | Alferness et al. | 607/4 |
| 5,810,887 | 9/1998 | Accorti, Jr. et al. | 607/122 |
| 5,814,081 | 9/1998 | Ayers et al. | 607/5 |
| 5,871,444 * | 2/1999 | Ouchi | 600/374 |
| 5,913,887 | 6/1999 | Michel | 607/123 |

* cited by examiner

Primary Examiner—Jeffrey R. Jastrzab (57) ABSTRACT

A flexible catheter shaft suitable for inserting into a body of a patient comprising a high torque transmission assembly of a slit tubular element that has either a plurality of slits or at least one continuously spiraling slit on said slit tubular element and has sufficient torque properties ensuring that a substantial fraction of the rotational and displacement forces provided along said flexible catheter shaft are translated to rotational and displacement forces at a distal end of said flexible catheter shaft.

18 Claims, 7 Drawing Sheets

HIGH TORQUE CATHETER AND METHODS THEREOF

FIELD OF THE INVENTION

The present invention generally relates to improved constructions for a high torque catheter. More particularly, this invention relates to methods and catheters for diagnosing and treating cardiac arrhythmias via a torque transmittable cardiovascular catheter by stimulating the human heart with pacing, cardioversion, defibrillation, and/or radiofrequency ablation therapy.

BACKGROUND OF THE INVENTION

Symptoms of abnormal heart rhythms are generally referred to as cardiac arrhythmias, with an abnormally rapid heart beat being referred to as tachycardia. The present invention is concerned with the treatment of tachycardias that are frequently caused by the presence of an "arrhythmogenic site" or "accessory atrioventricular pathway" close to the surface of the upper chambers of a heart. The heart includes a number of normal pathways that are responsible for the propagation of electrical signals from the upper chamber to the lower chamber necessary for performing normal systole and diastole functions. The presence of arrhythmogenic site or accessory pathway can bypass or short circuit the normal pathway, potentially resulting in very rapid heart contractions, referred to here as tachycardias.

Treatment of tachycardias may be accomplished by a variety of approaches, including drugs, surgery, implantable pacemakers/defibrillators, and catheter ablation. Catheter based radiofrequency ablation is generally performed after conducting an initial electrophysiology study where the locations of the arrhythmogenic site and/or accessory pathway are determined. Electrophysiology study and temporary defibrillator/cardioverter involve catheters having at least one electrode means for the delivery of low energy pacing pulses directly to the heart tissue at various intervals or frequencies in order to induce the arrhythmia. Once the arrhythmia is induced, it must be terminated by typically delivering a high-energy defibrillation shock across the patient's chest with paddles. A specific very high therapeutic voltage is required within the heart to terminate the induced arrhythmias. The voltage delivered through a conventional transthoracic defibrillator paddle from outside the body is substantially greater than the necessary therapeutic voltage because it needs to compensate for the energy losses through the skin and the thoracic cavity. An internal defibrillator/cardioverter from a catheter poses less risk and higher therapeutic efficiency.

A transvenous catheter that combines the functions of the rate sensing, pacing, and defibrillation has a plurality of electrodes on a distal portion. The catheter should have high torque so that it can be guided to the exact location of the heart tissue for pacing, cardioversion, defibrillation and/or radiofrequency ablation. The catheter should also be flexible enough for insertion into a body and have adequate surface for contacting the intracardiac tissues. Some examples of cardioverter and methods are U.S. Pat. Nos. 5,005,587 to Scott, 5,766,224 to Alferness et al., 5,814,081 to Ayers et al., 5,810,887 to Accorti, Jr. et al., and 5,913,887 to Michel. Because of the exact location requirements, the torque transmission properties of a catheter to ensure that a substantial fraction of the rotational and displacement forces provided along the catheter are translated to rotational and displacement forces at the distal end of said catheter become very important.

Another particular interest point to the present invention is radiofrequency (RF) ablation protocols that have proven to be highly effective in tachycardia treatment while exposing a patient to minimal side effects and risks. After a mapping study, an ablation catheter is usually introduced to the target heart chamber and is manipulated so that the ablation tip electrode lies exactly at the target tissue site. Radiofrequency energy or other suitable energy is then applied through the electrode to the cardiac tissue in order to ablate the tissue of arrhythmogenic site or the accessory pathway. By successfully destroying that tissue, the abnormal conducted signal patterns responsible for the tachycardia can be eliminated. In the case of atrial fibrillation (AFib), multiple arrhythmogenic sites and/or multiple accessory pathways exist. It becomes desirable that a long linear lesion or a broad lesion zone at the tissue contact sites to ensure appropriate energy delivery.

Scott in U.S. Pat. No. 5,005,587 discloses a braided electrode lead in an endocardial pacing and defibrillation catheter having an elongated hollow polyurethane shaft. Although providing good stiffness and biocompatibility, the polyurethane tube lacks sufficient translation between the rotational and displacement forces applied along the body of the polyurethane tube. Accorti Jr. et al. in U.S. Pat. No. 5,810,887 discloses a catheter having a braided wire section for torque transmission. For the purposes of cardioversion and defibrillation, the surface contact area becomes very critical. With regards to the braided wire section, only the outer radial surface of the braided section is employed in contacting a tissue. In other words, the effective tissue-contacting surface of wires in the braided wire section is sub-optimal as compared to an essentially flat surface. The braiding of wires also makes the braided wire section undesirably rigid.

Similarly, Michel in U.S. Pat. No. 5,913,887 discloses a transvenous device having three coil electrodes for cardioversion of atrial flutter or atrial fibrillation. The tissue-contacting surface area of a coil electrode is less than an essentially flat surface. The coil electrode also suffers a drawback of less torque transmission property. None of the conventional temporary catheters for cardioversion/defibrillation has a steerability property.

While cardioversion and defibrillation procedures using an existing catheter design have produced some promising results, the torque transmission properties, the effective tissue-contacting surfaces, and rigidity of a conventional catheter usually do not meet the clinical requirements. Therefore, there is an urgent clinical need to have a flexible catheter that also possess high torque transmitting property to be used in cardioversion and defibrillation procedures.

SUMMARY OF THE INVENTION

The present invention provides an improved high torque catheter that can be used in the procedures of stimulating the human heart with pacing, cardioversion, defibrillation and/or radiofrequency ablation therapy. It is one object of the present invention to provide a flexible catheter with high torque transmission properties. It is another object of the present invention to provide a flexible catheter with a slit tubular element that has a plurality of slit on said slit tubular element. It is still another object of the present invention to provide a flexible catheter with a slit tubular element that has at least one continuously spiraling slit on said slit tubular element. The word "slit" is defined as a straight or curved narrow cut or opening on a substrate in this patent application.

In one embodiment, a high torque catheter comprises a flexible catheter shaft having a distal shaft section, a proximal shaft section and at least one middle shaft section, wherein each shaft section has a distal end and a proximal end, and wherein the shaft section is secured to its adjacent shaft section, said flexible catheter shaft having at least one lumen extending between the distal end of the distal shaft section and the proximal end of the proximal shaft section. A handle may be secured at the proximal end of the proximal shaft section. The catheter further comprises at least one shaft section comprising a high torque transmission assembly for transmitting torque along said at least one shaft section, said high torque transmission assembly comprising a slit tubular element that has a plurality of slits on said slit tubular element and has sufficient torque properties ensuring that a substantial fraction of the rotational and displacement forces provided along said at least one shaft section are translated to rotational and displacement forces at the distal end of said shaft section of the flexible catheter shaft. The high torque catheter of the present invention is equally useful as either a non-energy delivery catheter or an energy delivery catheter.

In another embodiment, said high torque transmission assembly comprises a slit tubular element that has at least one continuously spiraling slit on said slit tubular element and has sufficient torque properties ensuring that a substantial fraction of the rotational and displacement forces provided along said at least one shaft section are translated to rotational and displacement forces at the distal end of said shaft section of the flexible catheter shaft, wherein the slit tubular element has a plurality of parallel slit members resulting from the at least one continuously spiraling slit.

In a preferred embodiment, the arrangement of said plurality of slits with respect to a longitudinal axis of said shaft section of the catheter may be selected from the group consisting of a perpendicular slit, an angled slit, a curved slit, and a combination of the above thereof. Furthermore, each of the plurality of slits has a slit starting point at an outer surface of said shaft section and two slit terminating points at said outer surface away from the slit starting point, wherein the distances from said slit starting point to each of the two slit terminating points are about equal. In a further embodiment, the at least one slit terminating point is coupled with a small circular hole for even stress release, especially when the slit tubular element is bent in one direction or the opposite direction.

In a particularly preferred embodiment, the slit tubular element of the high torque transmission assembly is embedded within an elastic membrane, is covered on an inner side of the slit tubular element, or is covered on an outer side of the slit tubular element by an elastic membrane. In one embodiment, the elastic membrane is to separate the interior lumen of the slit tubular element from an exterior surrounding of said slit tubular element. The elastic membrane may be selected from the group of elastic material or expandable membrane consisting of silicone, latex, polyurethane, thermoplastic elastomer such as Pebax brand polyether block amides, polyethylene balloon, cross-linked polyethylene balloon, permeable membrane, polyethylene terephthalate balloon, and the like. The slit tubular element may be made of a material selected from the group consisting of polypropylene, polysulfone, platinum, stainless steel, Nitinol, gold, silver, iridium, tungsten, and their mixture thereof.

The high torque catheter of the present invention further comprises a RF energy generator and an electrical conductor secured to said RF energy generator and said slit tubular element, wherein the electrical conductor is adapted for transmitting RF energy from said RF energy generator to the slit tubular element which is constructed of a conductive material. The high torque catheter further comprises at least one electrode mounted on the catheter shaft that is adjacent to the slit tubular element. The at least one electrode and/or the slit tubular element may be used for sensing, pacing, cardioversion, defibrillation and RF energy delivery.

In still another embodiment, the catheter further comprises a steering mechanism on the handle for deflecting the distal section of the catheter. One end of the steering wire is usually secured at said steering mechanism, while the other end is secured at a distal point on the inner side of the distal shaft section for deflecting the distal portion of said flexible high torque catheter. The catheter may further comprise a plurality of deflectable curves on the distal tip section of the catheter shaft being provided by the steering mechanism on the handle. By providing a steerable catheter with a plurality of deflectable curves, the catheter can fit the ventricle contours appropriately. The steering mechanism is well known to those who are skilled in the art. However, incorporation of a steering mechanism into a high torque catheter of the present invention is unobvious.

A method for operating a high torque catheter within a body of a patient may comprise the steps of: (a) percutaneously introducing the high torque catheter through an opening of the body of the patient; (b) approaching the high torque catheter to a target tissue of the patient by transmitting rotational and displacement forces through the at least one shaft section of the flexible catheter shaft; and (c) positioning the high torque catheter at the target tissue for diagnostic and/or therapeutic tissue treatment. Said high torque catheter comprises a flexible catheter shaft having a plurality of shaft sections, wherein at least one shaft section comprises a high torque transmission assembly for transmitting torque along said at least one shaft section, said high torque transmission assembly comprising a slit tubular element that has a plurality of slits on said slit tubular element and has sufficient torque properties ensuring that a substantial fraction of the rotational and displacement forces provided along said at least one shaft section are translated to rotational and displacement forces at a distal end of said shaft section.

The method and apparatus of the present invention have several significant advantages over known conventional catheters or techniques, particularly the flexible slit tubular element on at least one shaft section of the flexible catheter make the catheter particularly useful in procedures for stimulating the human heart with pacing, cardioversion, defibrillation, and/or radiofrequency ablation.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Figure 1:
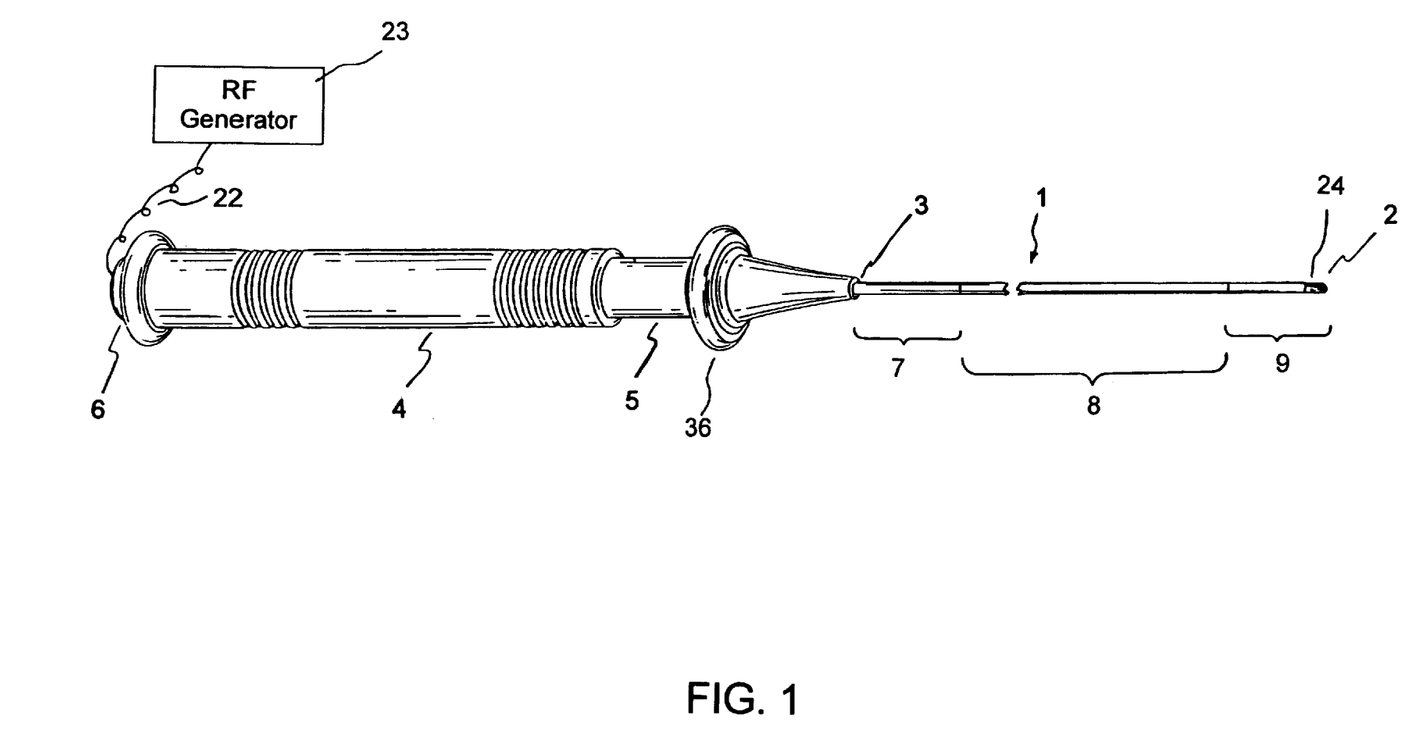
FIG. 1 is an overall view of a high torque catheter having a plurality of shaft sections and at least one slit tubular element constructed in accordance with the principles of the present invention.

What is shown in FIGS. 1 to 5 is a preferred embodiment of the present invention. FIG. 1 shows an overall view of a high torque catheter having a plurality of shaft sections and at least one slit tubular element of torque transmitting assembly constructed in accordance with the principles of the present invention. The flexible high torque catheter comprises a flexible catheter shaft 1 having a distal shaft section 9, a proximal shaft section 7 and a middle shaft section 8, wherein each shaft section has a distal end and a proximal end, wherein each shaft section is secured to its adjacent shaft section. Said catheter shaft has a distal end 2 and a proximal end 3. A handle 4 is secured at the proximal end 3 of the proximal shaft section 7. Said flexible catheter shaft 1 has at least one lumen 11 extending between the distal end 2 of the distal shaft section 9 and the proximal end 3 of the proximal shaft section 7.

At least one shaft section 7, 8, or 9 comprises a high torque transmission assembly for transmitting torque along said at least one shaft section, said high torque transmission assembly comprising a slit tubular element 18 that has a plurality of slits 12 on said slit tubular element 18 and has sufficient torque properties ensuring that a substantial fraction of the rotational and displacement forces provided along said at least one shaft section are translated to rotational and displacement forces at the distal end of said shaft section of the flexible catheter shaft 1.

The distal shaft section may be a fixed curve type or deflectable by employing a steering mechanism 5 at the handle 4. A push-pull plunger 36 is employed to deflect the distal shaft section 9 of the flexible catheter shaft 1. A connector 6 is secured at the proximal end of the handle 4. At least one electrode 24 available for electrophysiology use is disposed on the distal shaft section 9. The flexible catheter may further comprise a RF energy generator 23 and an electrical conductor 21, 22 secured to said RF energy generator 23 and said slit tubular element 18, 28, wherein the electrical conductor is adapted for transmitting RF energy from said RF energy generator to the at least one electrode 24 or the slit tubular element 18, 28.

Figure 2:
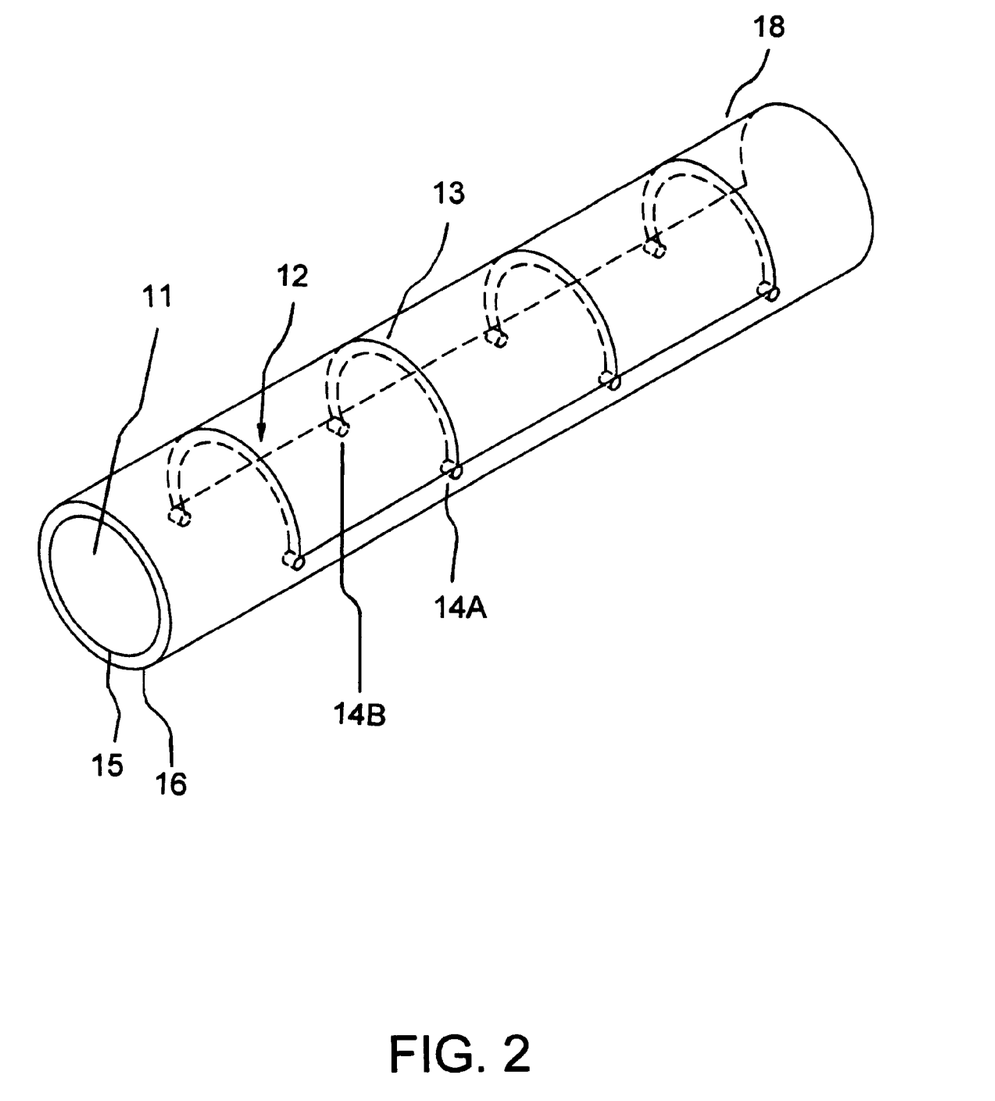
FIG. 2 is a perspective view of a preferred slit tubular element on a shaft section of the high torque flexible catheter at a non-bending state.

FIG. 2 shows a perspective view of a preferred slit tubular element 18 on a shaft section of the high torque flexible catheter at a non-bending state. A plurality of slits 12 is created along the slit tubular element 18. The slit can be created or arranged with respect to a longitudinal axis of said shaft section 7, 8, or 9 as selected from the group consisting of a perpendicular slit, an angled slit, a random slit, and a combination of the above thereof. The slit 12 can be created by a laser means, a mechanical means, or other suitable means.

Each of the plurality of slits 12 has a slit starting point 13 at an outer surface 16 of the shaft section and two slit terminating points 14A, 14B at the outer surface away from the slit starting point 13. At least one slit terminating point 14A, 14B may be coupled with a small circular hole as shown in FIG. 2. Said small circular hole is for stress release when the slit tubular element is in a deflectable state. Each slit may penetrate through the inner surface 15 of the slit tubular element 18. Each of the slit starting point 13, 13A, or 13B may be on the same side, on the opposite side, or randomly on the surface of the slit tubular element 18. This is to accommodate longitudinal torque transmission along the slit tubular element and deflectability in a plurality of directions of the distal shaft section of this flexible catheter.

Figure 3:
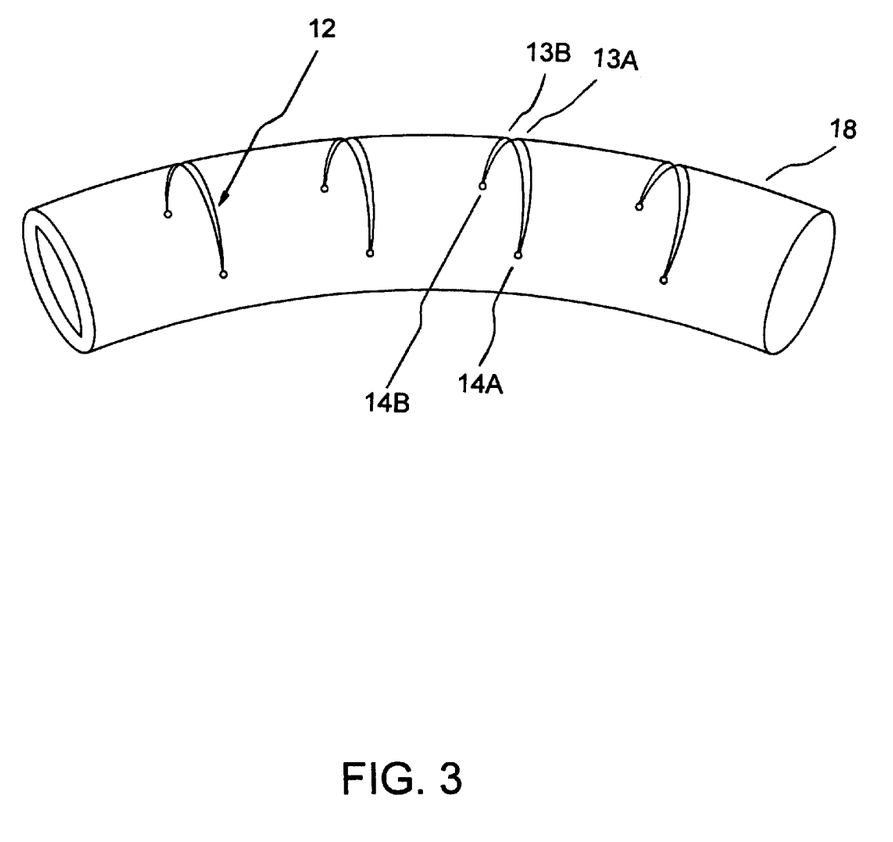
FIG. 3 is a perspective view of a preferred slit tubular element on a shaft section of the high torque flexible catheter at a bending state.

FIG. 3 shows a perspective view of a preferred slit tubular element on a shaft section of the high torque flexible catheter at a bending state. While the preferred slit tubular element 18 is capable for torque transmission, the element 18 can be bent depending on the slit starting side. When a slit tubular element 18 is bent, the slit starting points 13A, 13B on the opposite of the slit 12 facilitate deflectability.

Figure 4:
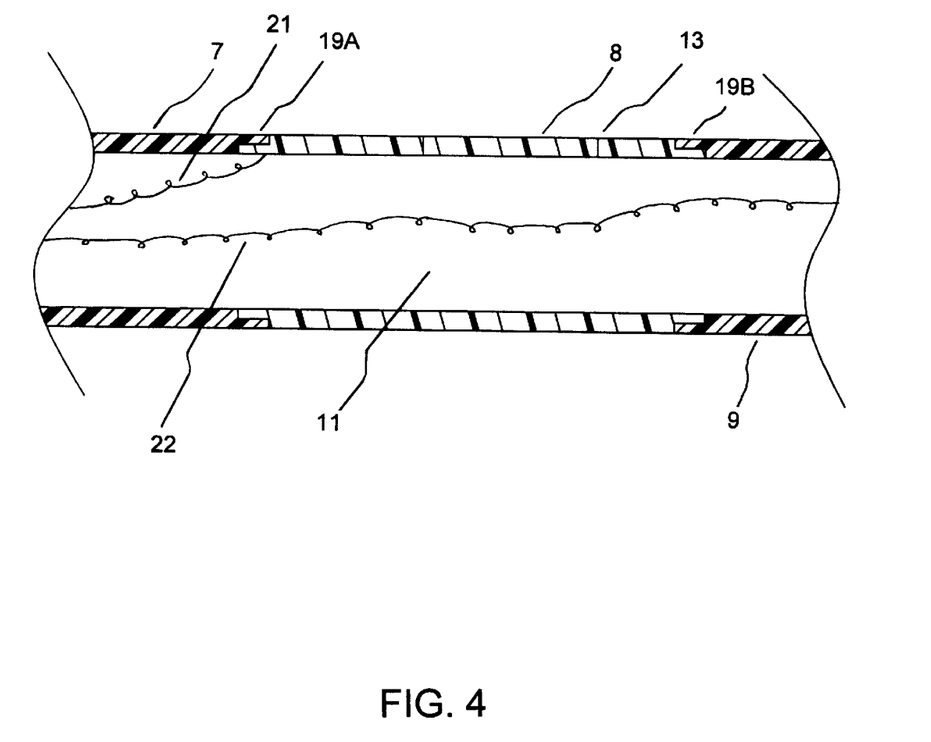
FIG. 4 is a cross sectional view of a middle shaft section having a slit tubular element at a non-bending state.
Figure 5:
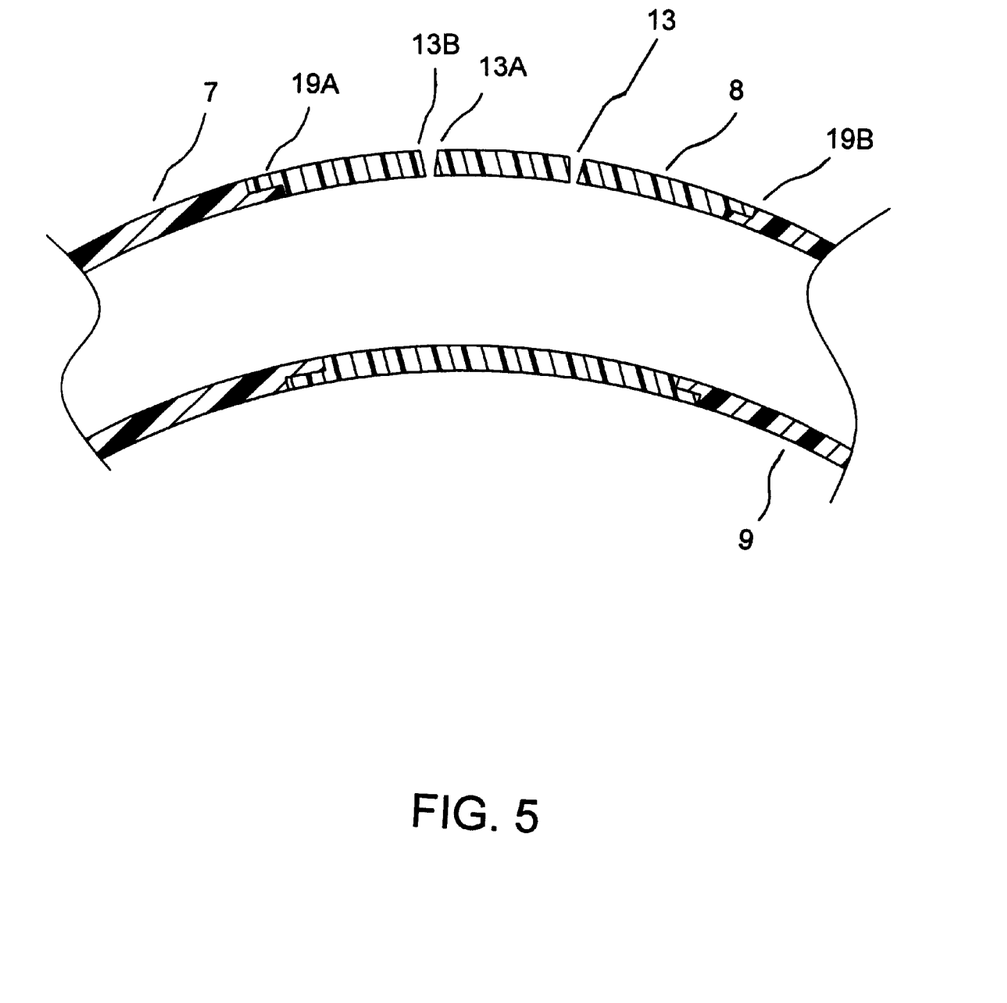
FIG. 5 is a cross sectional view of a middle shaft section having a slit tubular element at a bending state.

FIG. 4 shows a cross sectional view of a middle shaft section having a preferred slit tubular element of FIG. 2 at a non-bending state. A distal end of the proximal shaft section 7 is firmly secured to a proximal end of a middle shaft section 8 at a joint region 19A. Similarly, a proximal end of the distal shaft section 9 is firmly secured to a distal end of a middle section 8 at a joint region 19B. The two sections can generally be secured together by adhesion, welding, screwing or other suitable means. An electrical conductor 21, 22 passed through the lumen 11 of the flexible catheter 1 is adapted for transmitting electrical signal, energy, to and from an electrode means to an external electrical equipment for signal sensing, pacing, cardioversion, defibrillation or RF energy delivery. FIG. 5 shows a cross sectional view of a shaft section having a slit tubular element 18 of FIG. 4 at a bending or deflection state.

Figure 6:
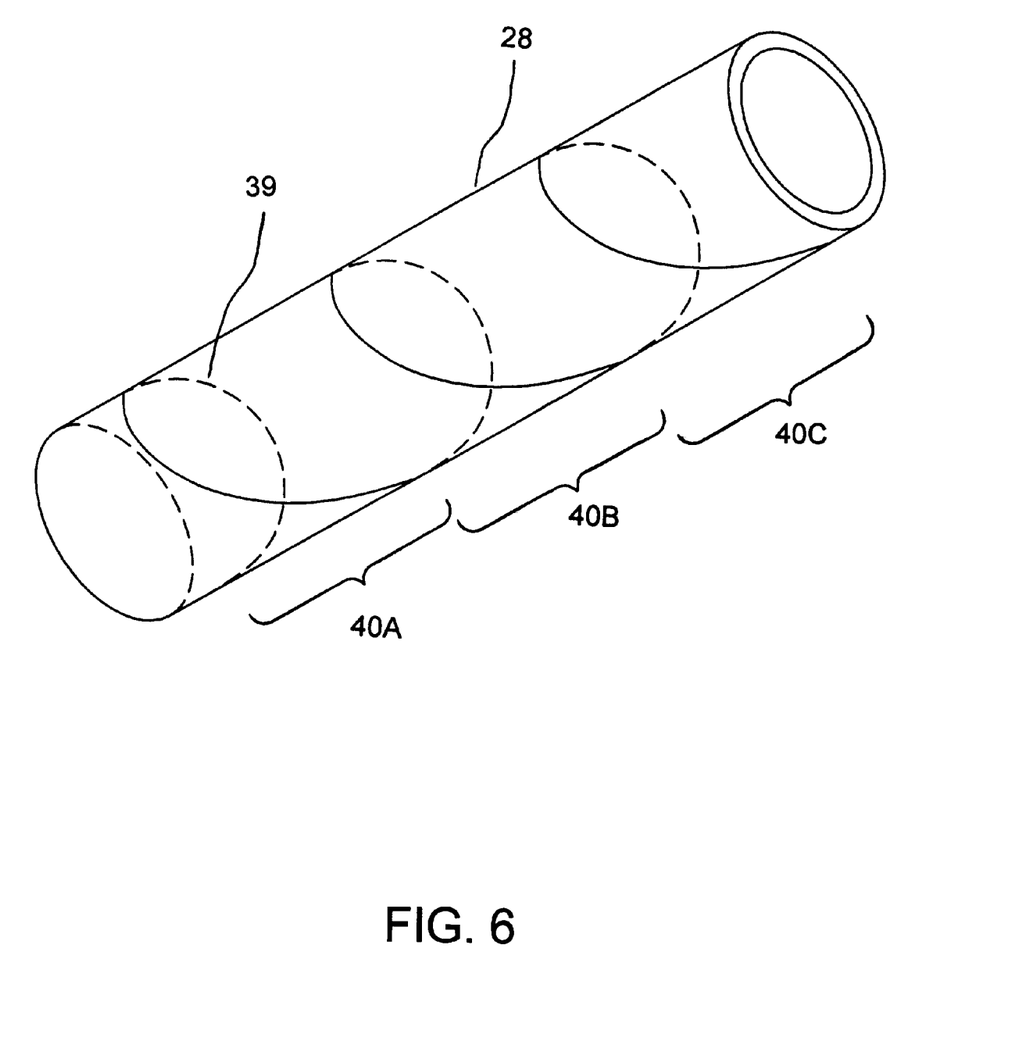
FIG. 6 is a perspective view of another preferred slit tubular element on a shaft section of the high torque flexible catheter at a non-bending state.

FIG. 6 shows a perspective view of another preferred slit tubular element on a shaft section of the high torque flexible catheter at a non-bending state. At least one shaft section 7, 8, 9 comprises a high torque transmission assembly for transmitting torque along the at least one shaft section. The high torque transmission assembly comprises a slit tubular element 28 that has at least one continuously spiraling slit 39 on said slit tubular element 28 and has sufficient torque properties ensuring that a substantial fraction of the rotational and displacement forces provided along the at least one shaft section are translated to rotational and displacement forces at the distal end of the shaft section of the flexible catheter shaft, wherein the slit tubular element has a plurality of parallel slit members such as pairs of 40A–40B or 40B–40C , resulting from the at least one continuously spiraling slit 39. In one embodiment, at least a portion 41 of at least one pair of adjacent slit members 40A–40B is secured together.

Figure 7:
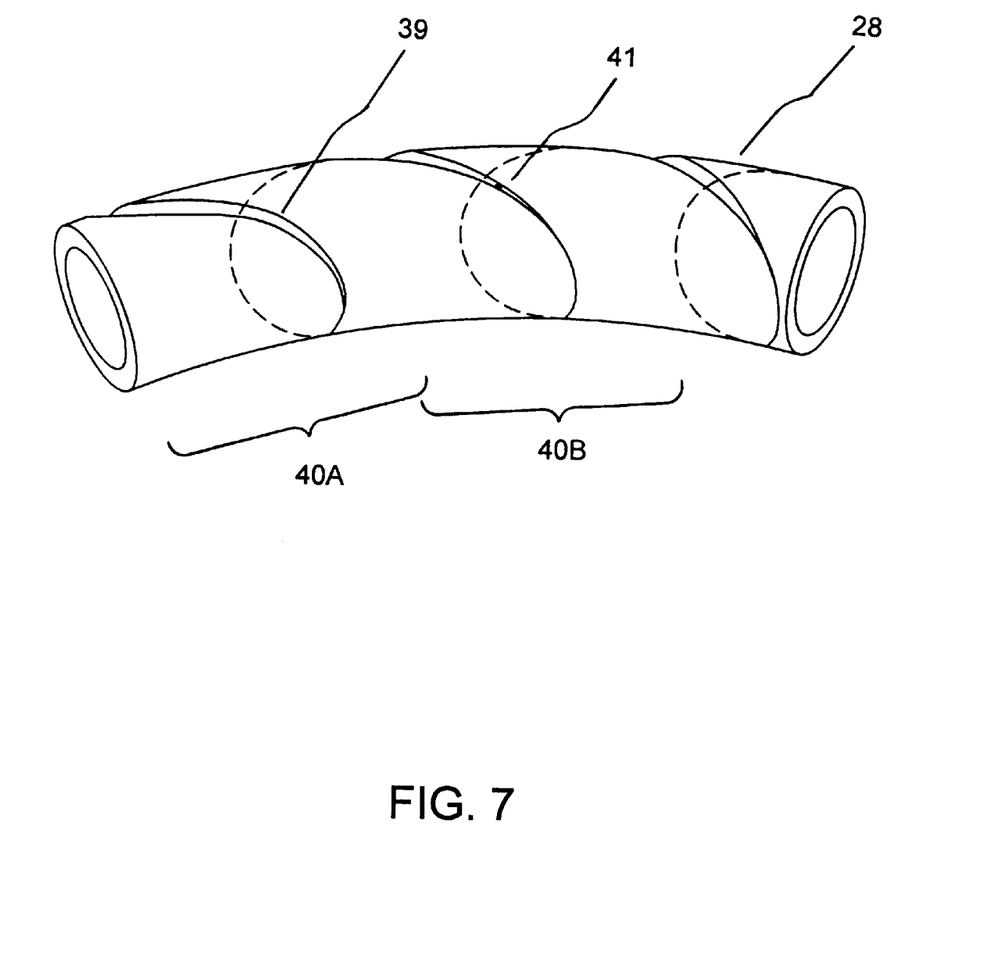
FIG. 7 is a perspective view of another preferred slit tubular element on a shaft section of the high torque flexible catheter at a bending state.

In a preferred embodiment, the slit tubular element 18, 28 of the high torque transmission assembly may be embedded within an elastic membrane, covered on an inner side of the slit tubular element, or covered on an outer side of the slit tubular element by an elastic membrane. In one further embodiment, the elastic membrane is to separate the interior lumen 11 of the slit tubular element 18, 28 from an exterior surrounding of the slit tubular element. The elastic membrane may preferably be selected from the group of elastic material, inflatable balloon, or expandable membrane consisting of silicone, latex, polyurethane, thermoplastic elastomer such as Pebax brand polyether block amides, polyethylene balloon, cross-linked polyethylene balloon, permeable membrane, polyethylene terephthalate balloon, and the like. The slit tubular element 18, 28 may be made of a material selected from the group consisting of polypropylene, polysulfone, platinum, stainless steel, Nitinol, gold, silver, iridium, tungsten, and their mixture thereof FIG. 7 is a perspective view of another preferred slit tubular element on a shaft section of the high torque flexible catheter of FIG. 6 at a bending or deflection state.

The slit tubular element 18 can only subject to the bending force or deflectability in the same direction of the slit 12 from the slit staring point 13 to the slit terminating points 14A, 14B. In the case of a slit tubular element 28 comprising a continuously spiraling slit 39, a plurality of securing portions or points 41 will make the slit tubular element 28 subject to the bending or deflection at a direction or a plane least resistance to restriction of the secured portion or portions 41.

From the foregoing, it should now be appreciated that an improved flexible catheter having high torque transmitting properties has been disclosed for cardiac and cardiovascular procedures. Particularly, the slit tubular element portion of the high torque flexible catheter is coupled with an electrical conductor for use in stimulating the human heart with pacing, cardioversion, defibrillation, and/or radiofrequency ablation therapy. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A high torque catheter comprising:
    a flexible catheter shaft having a distal shaft section, a proximal shaft section and a middle shaft section, wherein each shaft section has a distal end and a proximal end, said flexible catheter shaft having at least one lumen extending between the distal end of the distal shaft section and the proximal end of the proximal shaft section;
    a handle secured at the proximal end of the proximal shaft section; and
    at least one shaft section comprising a high torque transmission assembly for transmitting torque along said at least one shaft section, said high torque transmission assembly comprising a slit tubular element that has a plurality of slits on said slit tubular element, wherein arrangement of said plurality of slits with respect to a longitudinal axis of said shaft section is selected from the group consisting of an angled slit, a curved slit, and a combination of a perpendicular slit and an angled slit.

2. The high torque catheter of claim 1, wherein each of the plurality of slits has a slit starting point at an outer surface of said shaft section and two slit terminating points at said outer surface away from the slit starting point, each slit terminating point being coupled with a small circular hole.

3. The high torque catheter of claim 1, wherein the slit tubular element of the high torque transmission assembly is embedded within an elastic membrane.

4. The high torque catheter of claim 3, wherein the elastic membrane is selected from the group consisting of silicone, latex, polyurethane, thermoplastic elastomer, polyethylene balloon, cross-linked polyethylene balloon, permeable membrane, and polyethylene terephthalate balloon.

5. The high torque catheter of claim 1, wherein the slit tubular element of the high torque transmission assembly is covered on an external side or on an internal side of said slit tubular element by an elastic membrane.

6. The high torque catheter as in claim 1, wherein the slit tubular element is made of a material selected from the group consisting of platinum, stainless steel, nitinol, gold, silver, iridium, tungsten, and an alloy of their mixture.

7. The high torque catheter as in claim 1, further comprising at least one electrode mounted on the catheter shaft that is adjacent to the slit tubular element.

8. The high torque catheter as in claim 7, further comprising a RF energy generator and an electrical conductor secured to said RF energy generator and said slit tubular element, wherein the electrical conductor is adapted for transmitting RF energy from said RF energy generator to the at least one electrode or the slit tubular element.

9. The high torque catheter as in claim 1, further comprising a steering mechanism on the handle for deflecting the distal shaft section of the flexible catheter shaft.

10. A high torque catheter comprising:
    a flexible catheter shaft having a distal shaft section, a proximal shaft section and a middle shaft section, wherein each section has a distal end and a proximal end, said flexible catheter shaft having at least one lumen extending between the distal end of the distal shaft section and the proximal end of the proximal shaft section;
    a handle secured at the proximal end of the proximal shaft section; and
    at least one shaft section comprising a high torque transmission assembly for transmitting torque along said at least one shaft section, said high torque transmission assembly comprising a slit tubular element that has at least one continuously spiraling slit on said slit tubular element and has sufficient torque properties ensuring that a substantial fraction of the rotational and displacement forces provided along said at least one shaft section are translated to rotational and displacement forces at the distal end of said shaft section of the flexible catheter shaft, wherein the slit tubular element has a plurality of parallel slit members resulting from the at least one continuously spiraling slit, wherein at least a portion of at least one pair of adjacent slit members is secured together.

11. The high torque catheter of claim 10, wherein the slit tubular element of the high torque transmission assembly is embedded within an elastic membrane.

12. The high torque catheter of claim 11, wherein the elastic membrane is selected from the group consisting of silicone, latex, polyurethane, polyethylene balloon, cross-linked polyethylene balloon, permeable membrane, and polyethylene terephthalate balloon.

13. The high torque catheter of claim 10, wherein the slit tubular element of the high torque transmission assembly is covered by an elastic membrane, the elastic membrane separating an exterior of said slit tubular element from an interior of said slit tubular element.

14. The high torque catheter of claim 10, wherein the slit tubular element is made of a material selected from the group consisting of platinum, stainless steel, Nitinol, gold, silver, iridium, tungsten, and their mixture thereof.

15. The high torque catheter as in claim 10, further comprising at least one electrode mounted on the flexible catheter shaft that is adjacent to the slit tubular element.

16. The high torque as in claim 15, further comprising a RF energy generator and an electrical conductor secured to said RF energy generator and said slit tubular element, wherein the electrical conductor is adapted for transmitting RF energy from said RF energy generator to the at least one electrode or the slit tubular element.

17. The high torque catheter as in claim 10, further comprising a steering mechanism on the handle for deflecting the distal shaft section of the flexible catheter shaft.

18. A method for operating a high torque catheter within a body of a patient, the high torque catheter comprising a flexible catheter shaft having a plurality of shaft sections, wherein at least one shaft section comprises a high torque transmission assembly for transmitting torque along said at least one shaft section, said high torque transmission assembly comprising a slit tubular element that has a plurality of slits on said slit tubular element, wherein arrangement of said plurality of slits with respect to a longitudinal axis of said shaft section is selected from the group consisting of an angled slit, a curved slit, and a combination of a perpendicular slit and an angled slit;

the method comprising the steps of:
- (a) percutaneously introducing the high torque catheter through an opening of the body of the patient;
- (b) approaching the high torque catheter to a target tissue of the patient by transmitting rotational and displacement forces through the at least one shaft section of the flexible catheter shaft; and
- (c) positioning the high torque catheter at the target tissue for diagnostic and/or therapeutic tissue treatment.

\* \* \* \* \*